(12) United States Patent
Vanderpool et al.

(10) Patent No.: US 11,559,293 B1
(45) Date of Patent: Jan. 24, 2023

(54) APPARATUS FOR FACILITATING ACCESS TO ABDOMINAL CAVITY OF A PATIENT AND REMOVING LARGER CANCEROUS TUMORS

(71) Applicants: Charles H Vanderpool, Central Point, OR (US); Shaylene Tarvyd MacDonald, Torrance, CA (US); Scott Tarvyd MacDonald, Torrance, CA (US)

(72) Inventors: Charles H Vanderpool, Central Point, OR (US); Shaylene Tarvyd MacDonald, Torrance, CA (US); Scott Tarvyd MacDonald, Torrance, CA (US)

( * ) Notice: Subject to any disclaimer, the term of this patent is extended or adjusted under 35 U.S.C. 154(b) by 0 days.

(21) Appl. No.: 17/738,430

(22) Filed: May 6, 2022

Related U.S. Application Data (60) Provisional application No. 63/185,056, filed on May 6, 2021.

(51) Int. Cl.
*A61B 17/00* (2006.01)
*A61B 17/11* (2006.01)
*A61B 17/32* (2006.01)
*A61B 17/30* (2006.01)

(52) U.S. Cl.
CPC .... *A61B 17/00234* (2013.01); *A61B 17/1114* (2013.01); *A61B 17/320016* (2013.01); *A61B 2017/00287* (2013.01); *A61B 2017/306* (2013.01)

(58) Field of Classification Search
CPC ...... A61B 17/00234; A61B 17/320016; A61B 17/1114; A61B 2017/00287; A61B 10/0266; A61B 10/04
See application file for complete search history.

(56) References Cited

U.S. PATENT DOCUMENTS

| | | |
|---|---|---|
| 5,839,639 A | 11/1998 | Sauer |
| 6,083,241 A | 7/2000 | Longo et al. |
| 6,117,148 A | 9/2000 | Ravo et al. |
| 7,141,055 B2 | 11/2006 | Abrams et al. |
| 7,210,609 B2 | 5/2007 | Leiboff et al. |
| 8,361,090 B2 | 1/2013 | Belson |
| 10,806,457 B1 | 10/2020 | Vanderpool |

(Continued)

FOREIGN PATENT DOCUMENTS

WO    WO1991002491    3/1991

*Primary Examiner* — Wade Miles
(74) *Attorney, Agent, or Firm* — Eric Karich; Karich & Associates (57) ABSTRACT

An apparatus and method is provided for accessing an abdominal cavity of a patient via the anus for any number of surgical operations, e.g., colon cancer, appendectomy, lymph node biopsy, etc. The apparatus includes a tubular body that extends to an open end having a plurality of holes. The tubular body is inserted into the intestine of the patient, and a clamp is inserted through the tubular body of the apparatus and into the intestine. The clamp and the attached intestine is then pulled into the tubular body, so that the intestine can then be cut. The clamp and the adjacent intestine are then moved out of the tubular body so that the surgery may be performed through the intestine. The cut ends of the intestine can then be reattached (e.g., stapled, sutured, etc.) following completion of the surgery.

3 Claims, 11 Drawing Sheets

(56) References Cited

U.S. PATENT DOCUMENTS

| | | | |
|---|---|---|---|
| 2003/0158563 A1 | 8/2003 | McClellan et al. | |
| 2004/0015179 A1* | 1/2004 | Monassevitch | A61B 17/1114 606/153 |
| 2012/0010633 A1 | 1/2012 | Noda et al. | |
| 2012/0024935 A1* | 2/2012 | Shelton, IV | A61B 17/1155 227/176.1 |
| 2012/0029547 A1* | 2/2012 | Shelton, IV | A61B 17/1114 606/180 |
| 2014/0350566 A1* | 11/2014 | Emmanouilidis | A61B 17/1114 606/113 |
| 2019/0282235 A1* | 9/2019 | Aramaki | A61B 17/0469 |
| 2020/0253639 A1* | 8/2020 | Kim | A61B 17/29 |
| 2021/0212692 A1* | 7/2021 | Aramaki | A61B 17/1155 |
| 2022/0000483 A1* | 1/2022 | Aramaki | A61B 17/1114 |

\* cited by examiner

APPARATUS FOR FACILITATING ACCESS TO ABDOMINAL CAVITY OF A PATIENT AND REMOVING LARGER CANCEROUS TUMORS

CROSS-REFERENCE TO RELATED APPLICATIONS

This application for a utility patent claims the benefit of U.S. Provisional Application No. 63/185,056 filed May 6, 2021.

BACKGROUND OF THE INVENTION

Field of the Invention

The present invention relates generally to medical and laboratory equipment. More specifically, the present invention is an apparatus for facilitating access to an abdominal cavity of a patient and removing larger cancerous tumors.

Description of Related Art

Anastomosis refers to surgeons connecting two tube-like structures inside a human body. Patients may need anastomosis to join blood vessels or sections of the bowel. Existing techniques for facilitating access to abdominal cavity of a patient and removing larger cancerous tumors are deficient with regard to several aspects.

For instance, current technologies include the application of vacuum on the inside of an intraluminal anastomotic device. Further, current technologies do not include applying variable pressure or vacuum to an abdominal cavity of a patient. When the current technologies pull the intestine into a tube, current technologies may pull in folds of the surrounding intestines unless air is allowed in next to the mouth of the tube. Putting a small amount of air near the mouth of the tube will allow only the intended intestine to be drawn into the tube. As this occurs, the intestine is inflated on the inside of the tube. This blocks the view of the cameras necessary to do the operation/surgery.

A generally similar device is shown in Vanderpool et al., U.S. Pat. No. 10,806,457, which teaches a surgical tool that has an elongate tubular housing having an annular clamping region formed around an opening in the tubular housing. A vacuum source is operably engaged with the elongate tubular housing for providing a vacuum within the elongate tubular housing for drawing the damaged or diseased portion of a luminal body, such as an intestine, into the tubular housing. An elongate rod is provided having an annular clamping element shaped so that the intestine may be firmly clamped between the annular clamping element and the annular clamping region of the elongate tubular housing, so that the damaged or diseased portion of the intestine is entirely within the elongate tubular housing.

This device is not suitable, however, for handling large cancerous or otherwise damaged tissue. Therefore, there is a need for improved apparatus for facilitating access to abdominal cavity of a patient and removing larger cancerous tumors that may overcome one or more of the above-mentioned problems and/or limitations.

SUMMARY OF THE INVENTION

The present invention teaches certain benefits in construction and use which give rise to the objectives described below.

The present invention provides an apparatus and method for accessing an abdominal cavity of a patient via an intestine. The apparatus includes a tubular body that extends to an open end, the open end having a plurality of holes disposed around the open end. The tubular body is inserted into an intestine of the patient, and a clamp mounted on a control rod is inserted through the tubular body of the apparatus and into the intestine. The intestine is then clamped with the clamp, and clamp and the attached intestine are pulled into the tubular body of the apparatus via the control rod. The intestine is then cut, and the clamp and the adjacent intestine are them moved out of the tubular body of the apparatus, thus enabling the surgeon to laparoscopically access the abdominal cavity of the patient through the intestine, for performing any procedures required. The cut ends of the intestine may then be reattached.

A primary objective of the present invention is to provide an apparatus and method having advantages not taught by the prior art.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention.

DETAILED DESCRIPTION OF THE INVENTION

The present disclosure describes an apparatus for enabling access to an abdominal cavity through an intestine (i.e., colon) of a patient and removing larger cancerous tumors, either of the intestine or other organ in the abdominal cavity.

For purposes of this application, we refer to the removal of a tumor, but the term "tumor" is defined to include the removal of any deleterious material in the body, and is not limited to cancerous tissue.

Figure 1:
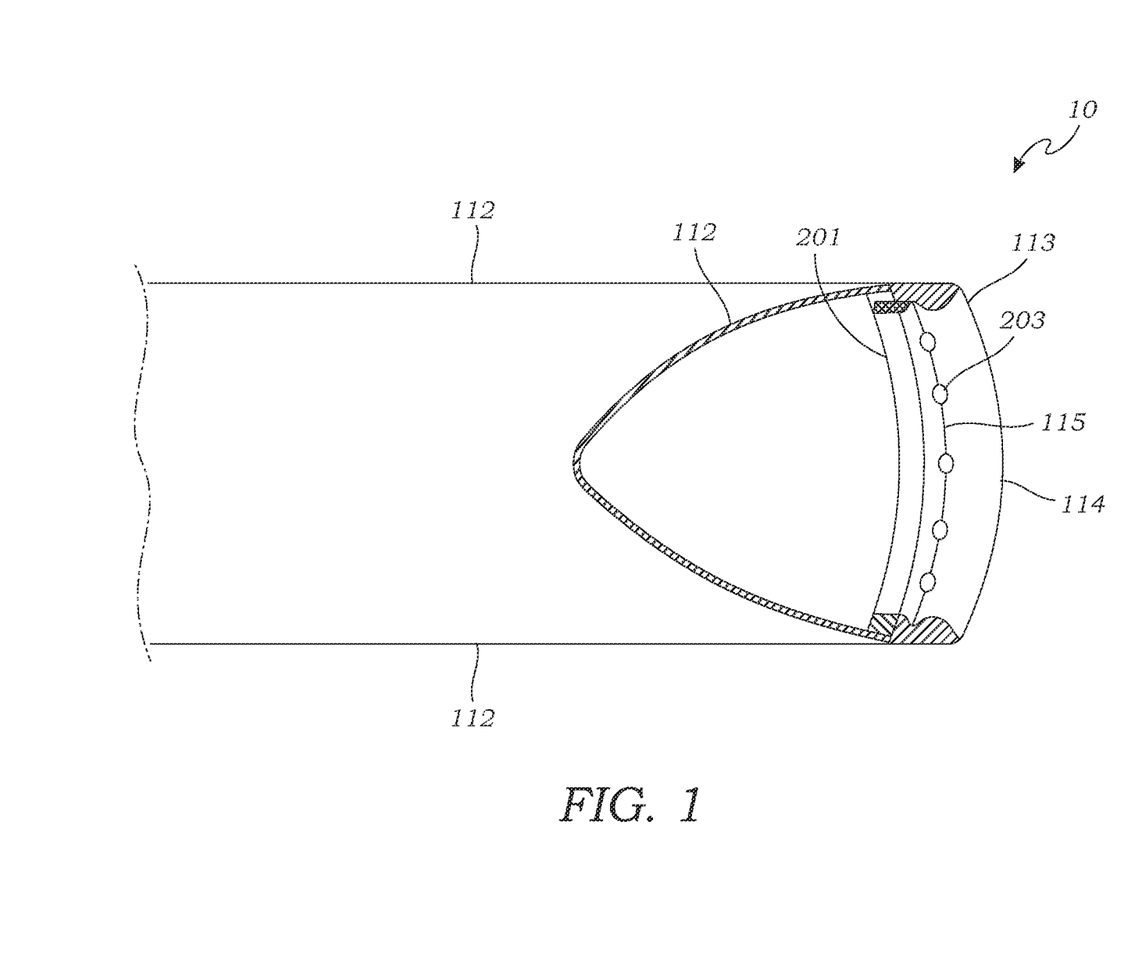
FIG. 1 is a cutaway view of a body of an apparatus according to one embodiment of the present invention and shown with air holes in a clamping region.

Referring now to figures, FIG. 1 is a cutaway view of a tubular body 112 of an apparatus 10 in accordance with one embodiment of the present invention. The tubular body 112 is sized and shaped to be inserted into an intestine of a patient, typically through the anus, with the term intestine being defined to include any other luminal structure in the body. The tubular body 112 extends to an open end 114 that includes a gripping element 203 for gripping the intestine 111 at the end 114. In this embodiment, the gripping element 203 is in the form of a plurality of holes which are in fluid communication with a vacuum source (not shown), i.e., a source of lower pressure which is lower than atmospheric pressure. While the holes and vacuum are used in this embodiment, other structures may be used, including mechanical mechanisms (e.g., arms, clamps, clips, etc.), chemical fasteners such as adhesives, other forms of pressure or vacuum, and non-mechanical means, and such alternative embodiments should be considered within the scope of the present invention.

As shown in FIG. 1, in this embodiment the holes 203 are positioned in a clamping region 115, in this embodiment the clamping region 115 being an annular construction that is formed as a female section (or a female depression) between a front lip 113 and an anvil 201, both of which may be annular in construction. These features enable the plurality of holes 203, in conjunction with the female clamping region 115 in this embodiment, to form a vacuum for removably clamping the intestine 111, as described in greater detail below.

Figure 2A:
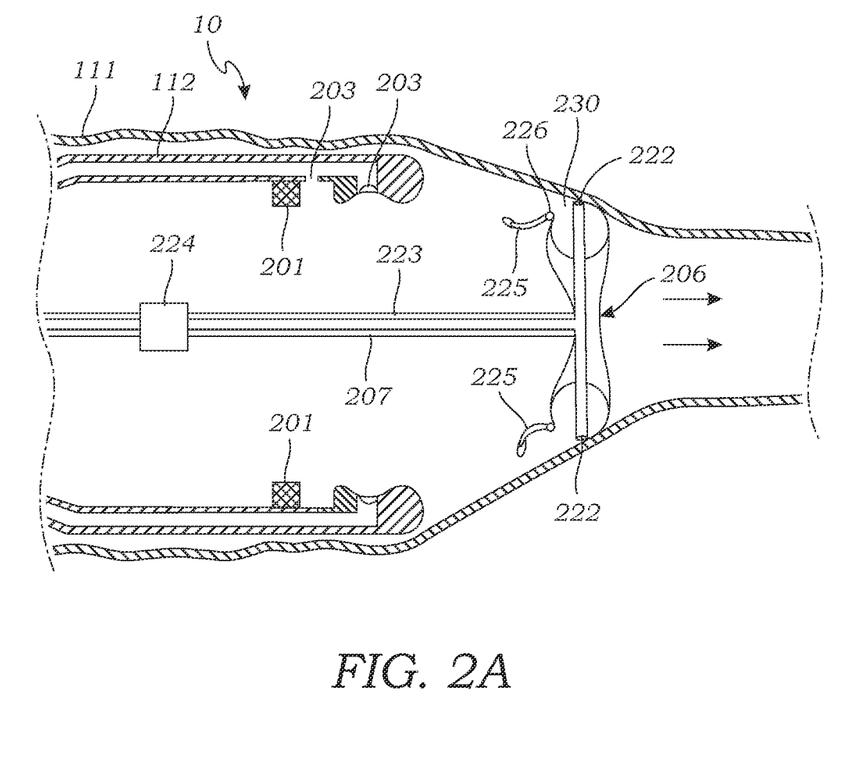
FIG. 2A is a schematic of a tip of the apparatus of FIG. 1 being inserted into a intestine, and illustrating an inflatable clamp being pushed through the apparatus and into the intestine for clamping a portion of the intestine.

FIG. 2A is a schematic of a tip of the apparatus 10 of FIG. 1 being inserted into a intestine 111, typically through an anus (not shown). The tubular body 112 is inserted into an intestine 111 of the patient so that the open end is near the tumor. For purposes of this application, the term "near" is defined to mean a suitable distance for performing the operation described below, as determined by the physician.

Figure 3:
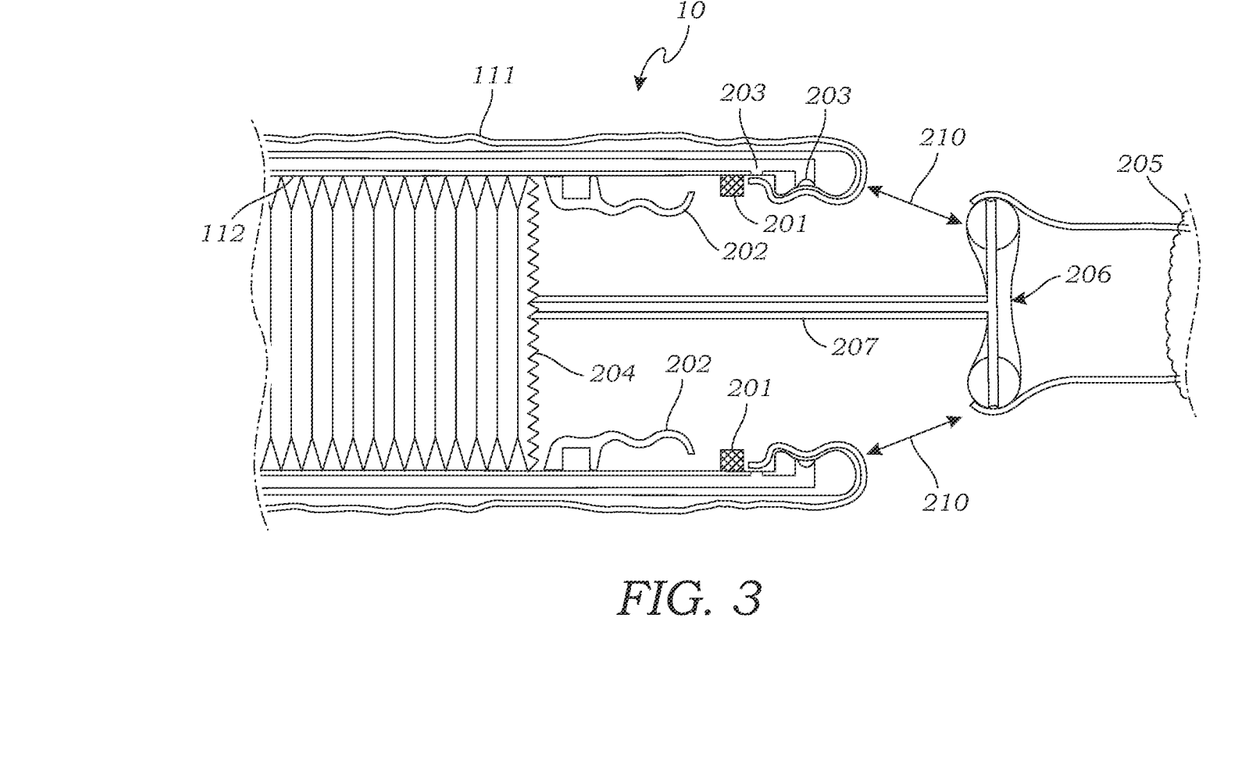
FIG. 3 is a cutaway view of the apparatus with a plastic bag in a collapsed position around a control rod of an inflatable clamp.

A clamp 206 is pushed through the apparatus 10 and into the intestine 111 for clamping a portion of the intestine 111. As shown in FIG. 2A, the clamp 206 (which in this embodiment is inflatable) is pushed up into the intestine 111 until it is adjacent to where an opening is desired (e.g., adjacent a tumor, as shown in FIG. 3 and discussed below), at which point a gripping element 222 is used to grip the intestine 111. In this embodiment, the gripping element includes a plurality of holes 222, in recessed space as described above with regards to the apparatus 10, are used to grip the intestine 111 with vacuum. As shown in FIG. 2A, the clamp has an annular outer surface 230 that includes the plurality of holes 222, and the clamp is attached to the intestine 111 via vacuum applied through the plurality of holes 222. For purposes of this application, the term "adjacent" is defined to mean a suitable distance for performing the operation described below, as determined by the physician. While this embodiment uses holes and vacuum, other means are also available (as discussed above with regards to element 203).

A control rod 207 of the inflatable clamp 206 may be used to manipulate the inflatable clamp 206, although other structures may be used in alternate embodiments. In this embodiment, the control rod 207 includes an inner conduit 223 that supplies the vacuum to the holes 222. In this embodiment, the control rod 207 includes a connector 224 which enables the inflatable clamp 206 to be removed from the remainder of the control rod 207 to facilitate access to the patient's abdomen, and the connector includes suitable valves that close off the vacuum source. While one form of control rod 207 is illustrated, the term "control rod" is defined to include any form of rod, tube, or control mechanism (e.g., a colonoscope) that can move the clamp 206 as required.

In this embodiment, the inflatable clamp 206 further includes locking arms 225, each attached to the inflatable clamp 206 with a hinge 226, said locking arms 225 functioning to clamp the intestine 111 against the inflatable clamp 206 when the control rod 207 is removed, so that the grip is not lost when the vacuum source is disconnected.

Once the inflatable clamp 206 has gripped the intestine 111, the inflatable clamp 206 and the intestine 111 may be pulled into the tube 112, where a cutting mechanism (not shown) may be used to cut the intestine 111, typically against the anvil 201, although it may be cut in any way known in the art. This process is shown and discussed in more detail in Vanderpool et al., U.S. Pat. No. 10,806,457, which is hereby incorporated by reference in its entirety.

Figure 2B:
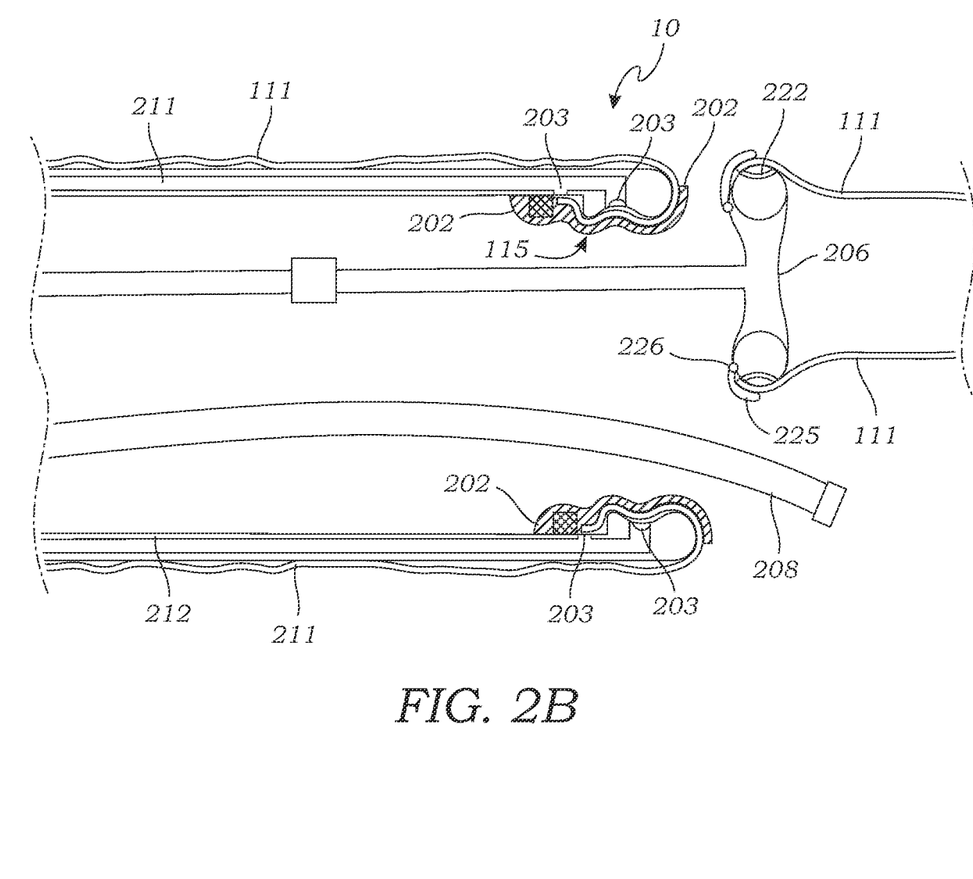
FIG. 2B is a schematic of the tip of the apparatus of FIG. 2A, illustrating the apparatus once the intestine has been cut adjacent the inflatable clamp, and further illustrating the inflatable clamp once it has been moved aside to allow a colonoscope to gain access to an abdomen through the intestine.

FIG. 2B is a schematic of the tip of the apparatus 10 of FIG. 2A, illustrating the apparatus 10 once the intestine 111 has been cut adjacent the inflatable clamp 206, and further illustrating the inflatable clamp 206 once it has been moved aside to allow a colonoscope 208 to gain access to an abdomen through the intestine 111.

As shown in FIG. 2B, the inflatable clamp 206 may be moved out of the way to allow access of the colonoscope 208 (or other surgical device needing to get into the abdomen) to the abdomen. As discussed above, the clamp 206 may be entirely removed, to allow even further access. Also shown in FIG. 2B, the intestine 111 adjacent the cut is held clamped against the holes 203 described above. An annular cover 202, in this case in the form of a protector cuff, may be placed over the intestine 111 and the anvil 201 at the clamping region 115. When the protector cuff 202 (such as a silicone cap or other resilient protective material) is in position, this region is covered and protected during the performance of the rest of the surgery.

FIG. 2B also illustrates the locking arms 225 once they have been closed to lock the intestine 111 in place.

FIG. 3 is a cutaway view of the apparatus with a plastic bag 204 in a collapsed position around the control rod 207 of the inflatable clamp 206, in accordance with some embodiments. Accordingly, the plastic bag 204 is in a ready position to be deployed. The covers 202 are shown exploded away from the clamping region 115, for clarity. Once the silicone cap is placed over an anvil 201 and the folded over intestine, the plastic bag (or bag) 204 is ready to deploy. The silicone cap is to protect the plastic bag 204 from the sharp edge of the anvil 201 and the folded over intestine from the bag 204 and the inflatable clamp control rod 207. The silicone cap serves a double duty protecting the bag from the sharp edge of the anvil 201 and the intestine 111 from the bag 204 and the control rod 207.

When the inflatable clamp 206 is positioned a short distance from the tube 112, a gap 210 is formed. The tubular bag 204 is positioned around the control rod 207, so that the tubular bag 204 may now be pulled over the inflatable clamp 206 that is holding the far end of the intestine 111.

Figure 4:
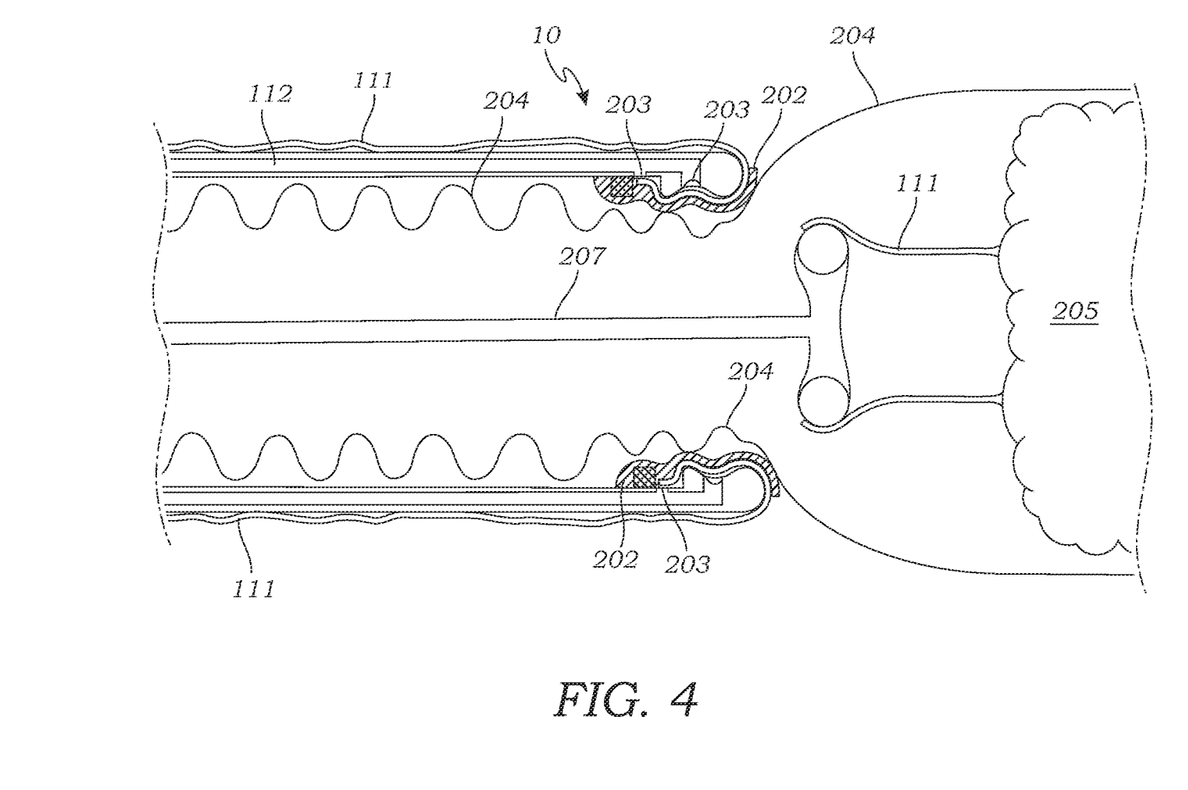
FIG. 4 illustrates the plastic bag deploying from inside the apparatus and enveloping a cancerous tumor.

FIG. 4 illustrates the container 204, in this case a plastic bag, being pulled out of the tube 112 over the end of the inflatable clamp 206 and encircling the intestine 111. As shown in FIG. 4, the pulling may be accomplished by laparoscopic movement, fluid movement, or any other means known in the art. Once in the bag 204, the tumor 205 may be cut up as needed so that it will fit into the tube 112 of the apparatus 10.

Figure 5:
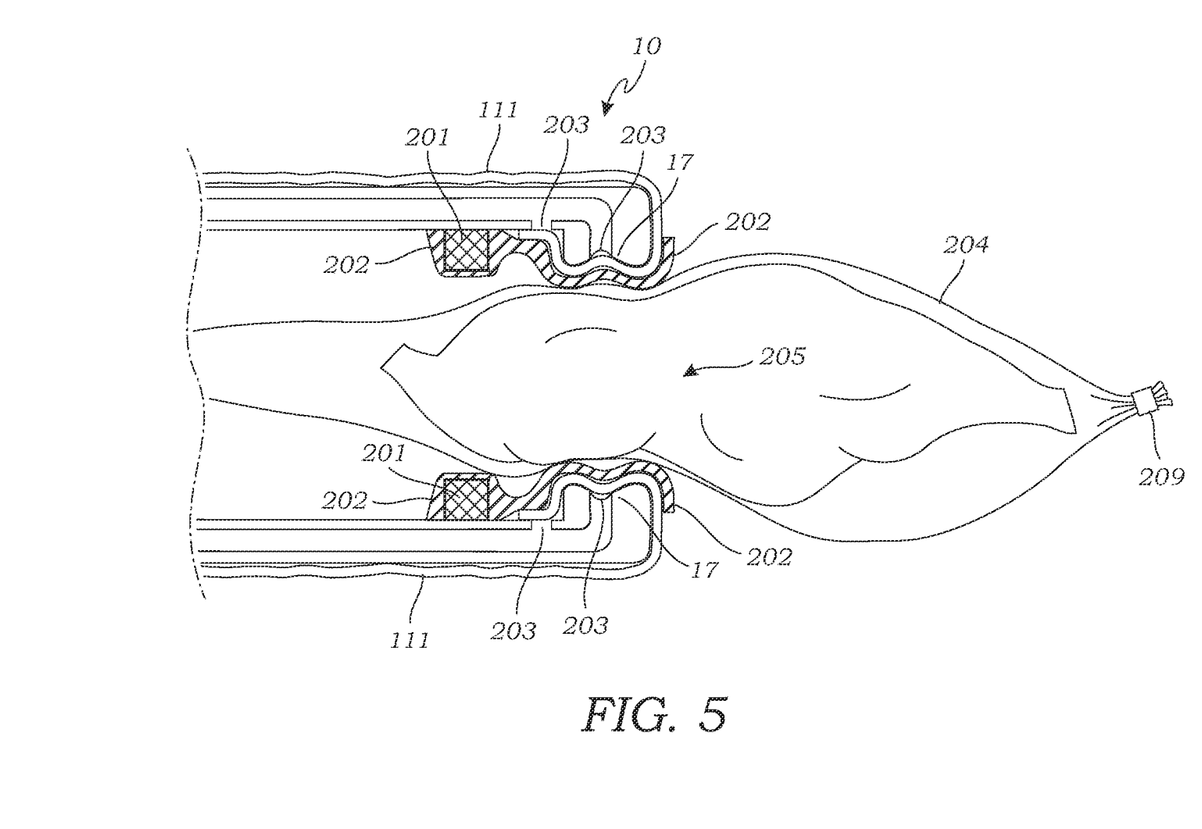
FIG. 5 illustrates a cancerous tumor enveloped in the plastic bag and being pulled into a mouth of the apparatus.

FIG. 5 illustrates the cancerous tumor 205 once the intestine 111 has been severed behind the tumor 205 and the plastic bag 204 has been sealed with a fastener 209 to contain the tumor 205. As shown in FIG. 5, the tumor 205 may then be pulled into a mouth of the apparatus 10. The cancerous section 205 of the intestine 111 may be completely contained within the tubular bag 204 (or plastic bag), greatly reducing the risk of the cancer spreading. Further, the tubular bag 204 and the intestine 111 may be pulled toward the tube 112. The cancerous section 205 of the intestine 111 is now inside of the tubular bag (or a long tubular sealed bag) 204.

Figure 6:
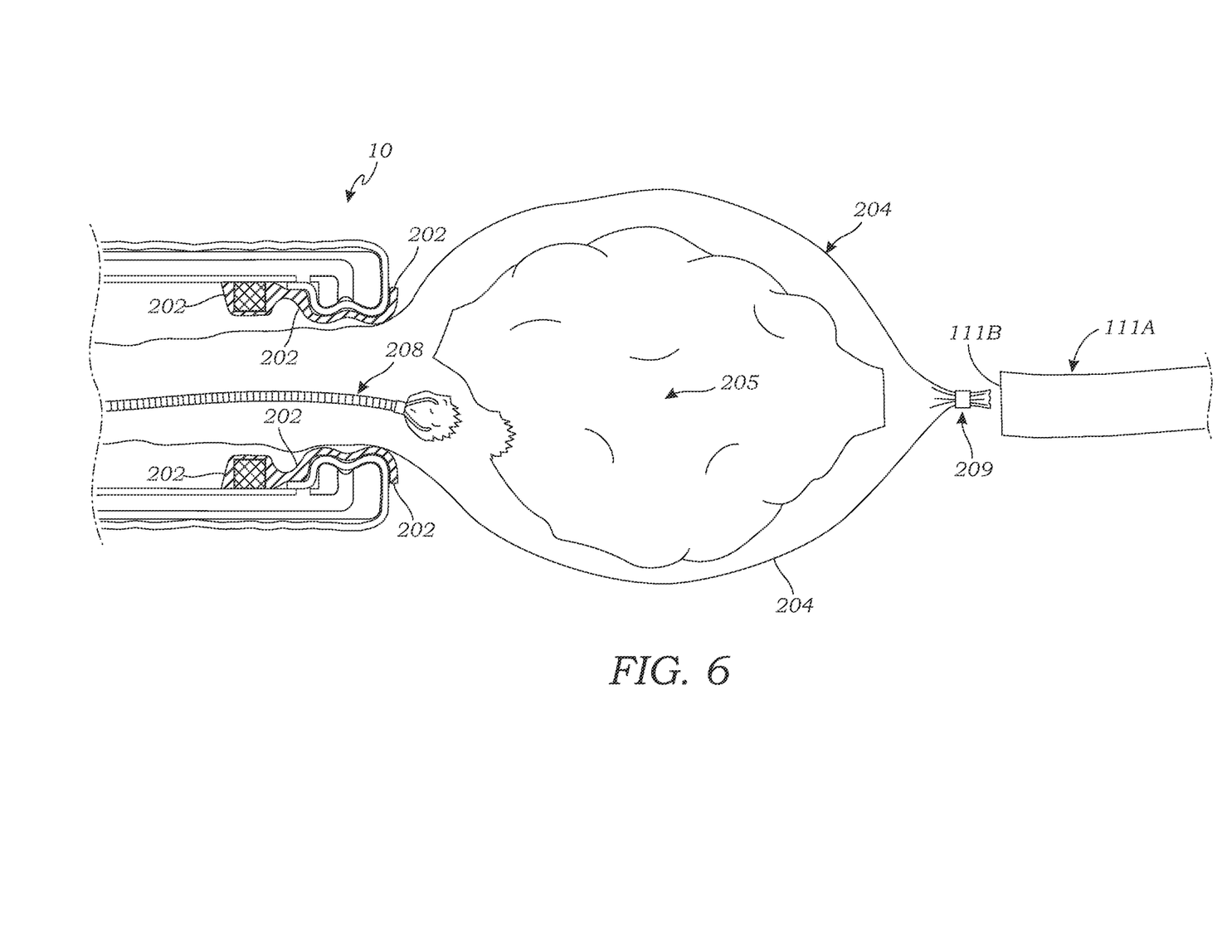
FIG. 6 illustrates the plastic bag enveloping the cancerous tumor too large to fit into the mouth of the apparatus.

FIG. 6 illustrates the plastic bag 204 enveloping the cancerous tumor 205 that is too large to fit into the mouth of the apparatus 10. Accordingly, the tumor 205 can be cut down, inside the bag (or the deployable plastic bag) 204, to a size small enough to pass through the mouth of the apparatus 10.

FIG. 6 also illustrates a far end of the intestine 111A, which is the rest of the intestine beyond the tumor. This illustrates the cut end 111B, from when the intestine is separated from the tumor.

Figure 7:
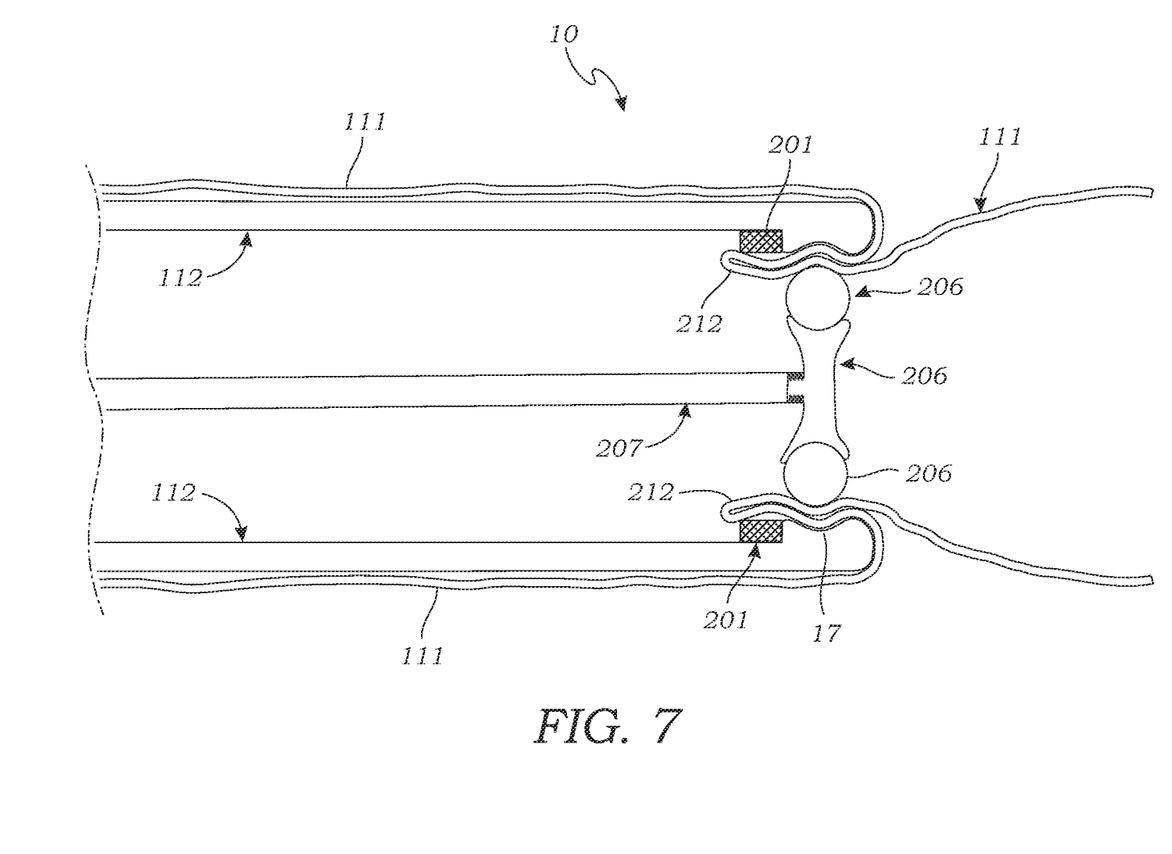
FIG. 7 illustrates the apparatus ready to cut a very small fold over on the intestine to allow further access.

FIG. 7 illustrates the apparatus 10 being used in another manner, to cut a very small fold over on the intestine 111 to allow further access. Accordingly, the small folded-over section, of the intestine 111, may be cut to allow for either abdominal access or the enveloping of larger cancers.

Figure 8:
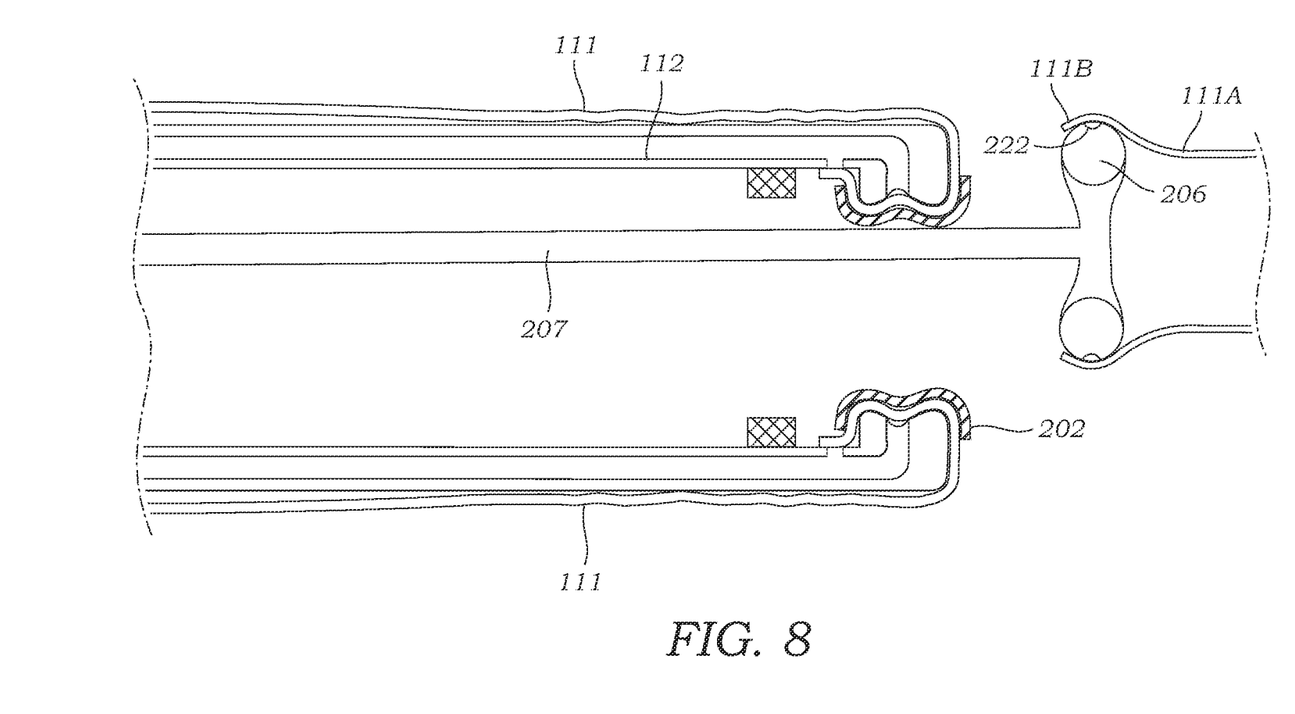
FIG. 8 illustrates the apparatus ready for access by a colonoscope.

FIG. 8 illustrates the apparatus 10 ready for access by a colonoscope or other tools. Once the tubular bag 204 and the intestine 111 are removed, the inflatable clamp 206 is reintroduced into the tube 112 and pushed into the abdomen. Further, the laparoscopic arms find the far cut end 111B of the intestine 111A and place it back on the inflatable clamp 206. Once a vacuum is induced in the inflatable clamp 206 and the far cut end of the intestine 111 is pulled toward the near cut end of the intestine 111, that is being held within the female section (or female clamp area) 115. Once the inflatable clamp 206 is seated back in a clamping region 115 (or female section) and inflated, the ends (such as the far ends and the near cut end) of the intestine 111 may be adjusted and re-cut if necessary. Further, the intestine 111 may be sutured back together.

In further embodiments, the apparatus may be configured for facilitating access to the abdominal cavity. Further, for accessing the abdominal cavity, a very small section of the intestine 111 is cut, as shown in FIG. 7, similar to the above system for placing a bag around a tumor-involved section of the intestine 111. For access, the far intestinal section is pushed out of the tube 112 leaving the gap 210 (as shown in FIG. 8). The gap 210 in the intestine may be used as a port for access to the abdomen. Further, the intestine, that may be folded into the tube 112, needs to be protected. To protect the intestine, small air holes are ported into the female land (female section) 115 and under the anvil 201 (or cutting anvil). When the intestinal cutter is done cutting, the anvil 201 is moved out of the way. As the anvil 201 is moved out of the way, a vacuum is induced in the air holes under the anvil 201. This may draw the intestine 111 down into the corner the anvil 201 was in. Further, the anvil 201 may include a metallic object the cutting knife works against to cut the intestine 111.

In further embodiments, disclosed herein is a system configured for facilitating access to abdominal cavity of a patient and removing larger cancerous tumors. Accordingly, the system may include a communication device, a processing device, and a storage device. Further, the processing device may be communicatively coupled to the vacuum source. Further, the vacuum source may be configured for inducing vacuum at the holes 203. Further, the communication device may be configured for receiving a pressure input associated with the vacuum source from at least one user device. Further, the at least one user device may include a smartphone, a laptop, a personal computer, a tablet, and so on. Further, the at least one user device may be associated with at least one user. Further, the at least one user may include a surgeon, a physician, a healthcare service provider, etc. Further, the communication device may be configured for transmitting a pressure value to the vacuum source. Further, the pressure value may be associated with the vacuum. Further, the processing device may be configured for analyzing the pressure input to determine the pressure value. Further, the storage device may be configured for storing the pressure input and the pressure value.

Figure 9:
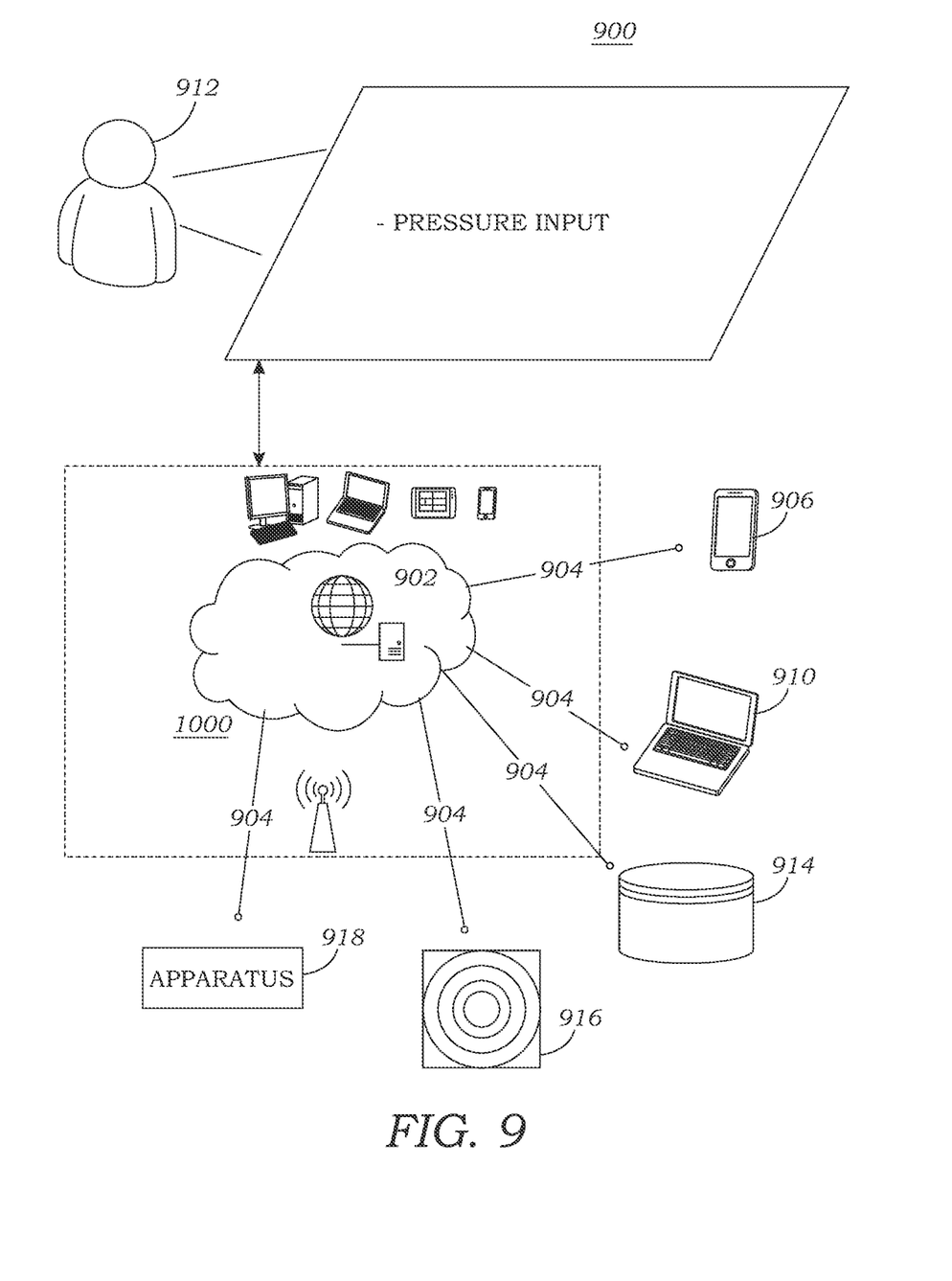
FIG. 9 is an illustration of an online platform consistent with various embodiments of the present disclosure.

FIG. 9 is an illustration of an online platform 900 consistent with various embodiments of the present disclosure. By way of non-limiting example, the online platform 900 for facilitating access to abdominal cavity of a patient and removing larger cancerous tumors may be hosted on a centralized server 902, such as, for example, a cloud computing service. The centralized server 902 may communicate with other network entities, such as, for example, a mobile device 906 (such as a smartphone, a laptop, a tablet computer, etc.), other electronic devices 910 (such as desktop computers, server computers, etc.), databases 914, sensors 916, and an apparatus 918 (such as an apparatus for facilitating access to abdominal cavity of a patient and removing larger cancerous tumors) over a communication network 904, such as, but not limited to, the Internet. Further, users of the online platform 900 may include relevant parties such as, but not limited to, end-users, medical healthcare providers, surgeons, and administrators. Accordingly, in some instances, electronic devices operated by the one 5 or more relevant parties may be in communication with the online platform 900.

A user 912, such as the one or more relevant parties, may access the online platform 900 through a web-based software application or browser. The web-based software application may be embodied as, for example, but not be limited to, a website, a web application, a desktop application, and a mobile application compatible with a computing device 1000.

Figure 10:
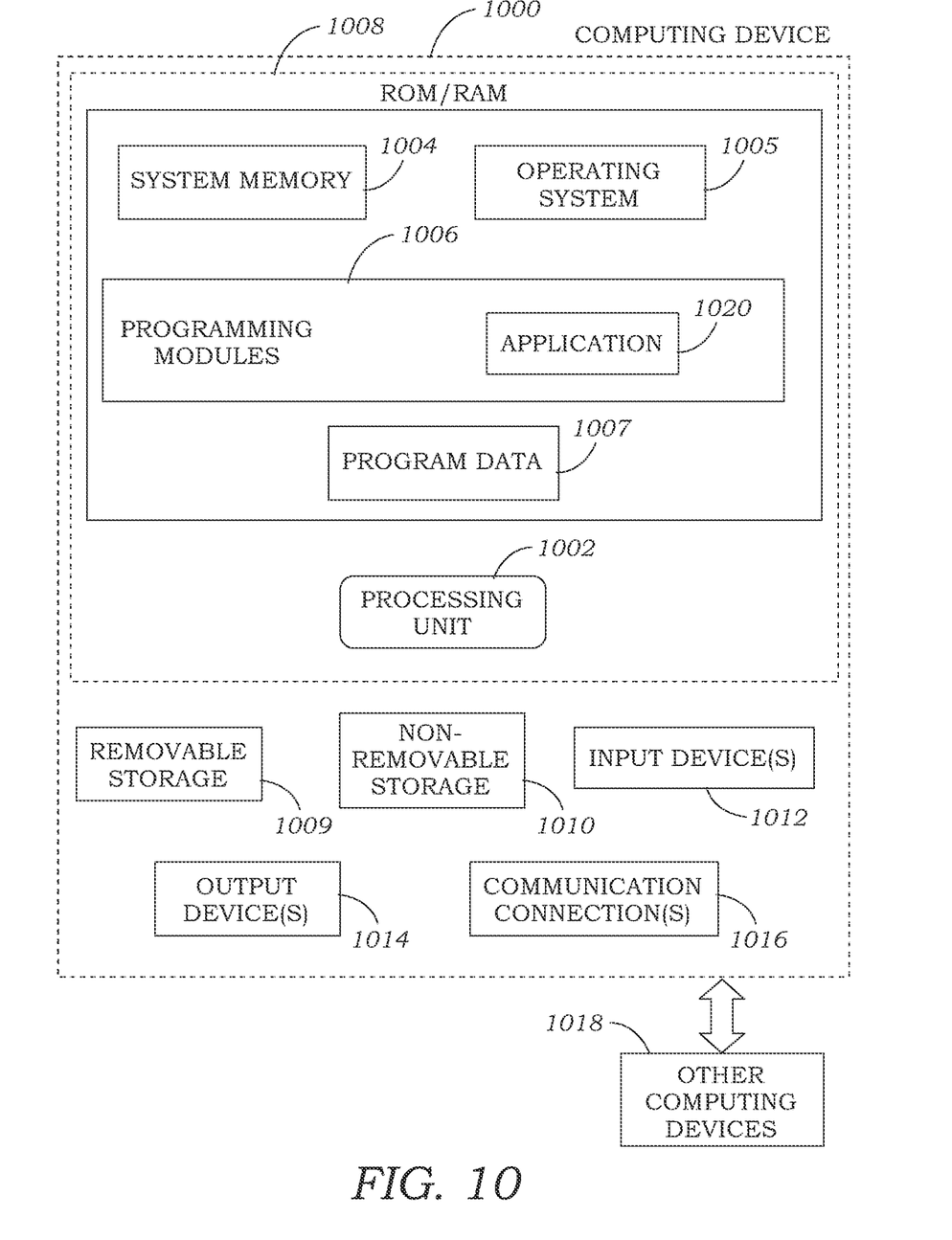
FIG. 10 is a block diagram of a computing device for implementing the methods disclosed herein.

With reference to FIG. 10, a system consistent with an embodiment of the disclosure may include a computing device or cloud service, such as computing device 1000. In a basic configuration, computing device 1000 may include at least one processing unit 1002 and a system memory 1004. Depending on the configuration and type of computing device, system memory 1004 may comprise, but is not limited to, volatile (e.g. random-access memory (RAM)), non-volatile (e.g. read-only memory (ROM)), flash memory, or any combination. System memory 1004 may include operating system 1005, one or more programming modules 1006, and may include a program data 1007. Operating system 1005, for example, may be suitable for controlling computing device 1000's operation. Furthermore, embodiments of the disclosure may be practiced in conjunction with a graphics library, other operating systems, or any other application program and is not limited to any particular application or system. This basic configuration is illustrated in FIG. 10 by those components within a dashed line 1008.

Computing device 1000 may have additional features or functionality. For example, computing device 1000 may also include additional data storage devices (removable and/or non-removable) such as, for example, magnetic disks, optical disks, or tape. Such additional storage is illustrated in FIG. 10 by a removable storage 1009 and a non-removable storage 1010. Computer storage media may include volatile and nonvolatile, removable and non-removable media implemented in any method or technology for storage of information, such as computer-readable instructions, data structures, program modules, or other data. System memory 1004, removable storage 1009, and non-removable storage 1010 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1000. Any such computer storage media may be part of device 1000. Computing device 1000 may also have input device(s) 1012 such as a keyboard, a mouse, a pen, a sound input device, a touch input device, a location sensor, a camera, a biometric sensor, etc. Output device(s) 1014 such as a display, speakers, a printer, etc. may also be included. The aforementioned devices are examples and others may be used.

Computing device 1000 may also contain a communication connection 1016 that may allow device 1000 to communicate with other computing devices 1018, such as over a network in a distributed computing environment, for example, an intranet or the Internet. Communication connection 1016 is one example of communication media. Communication media may typically be embodied by computer-readable 5 instructions, data structures, program modules, or other data in a modulated data signal, such as a carrier wave or other transport mechanism, and includes any information delivery media.

The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 1004, including operating system 1005. While executing on processing unit 1002, programming modules 1006 (e.g., application 1020 such as a media player) may perform processes including, for example, one or more stages of methods, algorithms, systems, applications, servers, databases as described above. The aforementioned process is an example, and processing unit 1002 may perform other processes.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the disclosure may 5 also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process.

Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Furthermore, although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

The terms "computer," "computer device," and "server" as used herein, refers to a device and/or system of devices that include at least one computer processing element, e.g., a central processing unit (CPU), and some form of computer memory having a capability to store data. The computer may comprise hardware, software, and firmware for receiving, storing, and/or processing data as described below. For example, a computer may comprise any of a wide range of digital electronic devices, including, but not limited to, a server, a desktop computer, a laptop, a smart phone, a tablet, or any form of electronic device capable of functioning as described herein.

The term "database" as used herein, refers to any form of one or more (or combination of) relational databases, object-oriented databases, hierarchical databases, network databases, non-relational (e.g. NoSQL) databases, document store databases, in-memory databases, programs, tables, files, lists, or any form of programming structure or structures that function to store data as described herein.

The term "computer memory" as used herein refers to any tangible, non-transitory storage that participates in providing instructions to a processor for execution. Such a medium may take many forms, including but not limited to, non-volatile media, volatile media, and any equivalent media known in the art. Non-volatile media includes, for example, ROM, magnetic media, and optical storage media. Volatile media includes, for example, DRAM, which typically serves as main memory. Common forms of computer memory include, for example, hard drives and other forms of magnetic media, optical media such as CD-ROM disks, as well as Various forms of RAM, ROM, PROM, EPROM, FLASH-EPROM, solid state media such as memory cards, and any other form of memory chip or cartridge, or any other medium from which a computer can read. While several examples are provided above, these examples are not meant to be limiting, but illustrative of several common examples, and any similar or equivalent devices or systems may be used that are known to those skilled in the art.

The title of the present application, and the claims presented, do not limit what may be claimed in the future, based upon and supported by the present application. Furthermore, any features shown in any of the drawings may be combined with any features from any other drawings to form an invention which may be claimed.

As used in this application, the words "a," "an," and "one" are defined to include one or more of the referenced item unless specifically stated otherwise. The terms "approximately" and "about" are defined to mean+/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by claims made to the invention.

What is claimed is:

1. A method for accessing an abdominal cavity of a patient via an intestine for removing a tumor, the method comprising the steps of:
    providing an apparatus that includes a tubular body that extends to an open end, the open end having a plurality of holes disposed around the open end;
    inserting the tubular body into an intestine of the patient so that the open end is near the tumor;
    inserting a clamp mounted on a control rod through the tubular body of the apparatus and into the intestine, until the clamp is positioned adjacent the tumor;
    positioning a flexible bag around the control rod of the clamp;
    clamping the intestine with the clamp;
    pulling the clamp and the attached intestine into the tubular body of the apparatus via the control rod;
    cutting the intestine adjacent the clamp and above the tumor;
    moving the clamp and the adjacent intestine out of the tubular body of the apparatus;
    laparoscopically removing the tumor through the intestine by pulling the flexible bag up over the clamp and the tumor, fastening the flexible bag closed above the tumor, so that the flexible bag contains the tumor, and removing the flexible bag and the tumor through the tubular body of the apparatus; and
    reattaching cuts ends of the intestine.

2. The method of claim 1, wherein the clamp has an annular outer surface that includes a plurality of holes, and the clamp is attached to the intestine via vacuum applied through the plurality of holes.

3. The method of claim 1, wherein the clamp has a plurality of arms which can clamp the intestine.

* * * * *